United States Patent [19]

Wichterle

[11] 3,971,376

[45] July 27, 1976

[54] METHOD AND APPARATUS FOR INTRODUCING FLUIDS INTO THE BODY

[75] Inventor: Otto Wichterle, Prague, Czechoslovakia

[73] Assignee: Ceskoslovenska akademie ved, Prague, Czechoslovakia

[22] Filed: Oct. 2, 1974

[21] Appl. No.: 511,428

Related U.S. Application Data

[63] Continuation-in-part of Ser. No. 335,745, Feb. 26, 1973, abandoned.

[52] U.S. Cl. .................. 128/260; 128/272
[51] Int. Cl.² .......................... A61M 7/00
[58] Field of Search ................. 128/260, 272

[56] References Cited
UNITED STATES PATENTS

| | | | |
|---|---|---|---|
| 1,434,531 | 11/1922 | Cyrenius | 128/272 |
| 2,663,461 | 12/1953 | Brown | 128/272 |
| 3,279,996 | 10/1966 | Long, Jr. et al. | 128/272 |
| 3,310,051 | 3/1967 | Schultz | 128/216 |
| 3,313,289 | 4/1967 | Kapral | 3/1 X |
| 3,520,949 | 7/1970 | Shepherd et al. | 3/1 UX |
| 3,527,220 | 9/1970 | Summers | 128/260 |
| 3,583,387 | 6/1971 | Garner | 128/1 R |
| 3,640,269 | 2/1972 | Delgado | 128/260 X |
| 3,664,341 | 5/1972 | Gordon | 128/271 |
| 3,731,681 | 5/1973 | Blackshear et al. | 3/1 X |
| 3,765,414 | 10/1973 | Arlen | 128/2 F X |
| 3,832,458 | 8/1974 | Merrill | 128/260 |
| 3,845,770 | 11/1974 | Higuchi et al. | 128/260 |

Primary Examiner—Aldrich F. Medbery
Attorney, Agent, or Firm—Murray Schaffer

[57] ABSTRACT

Method and apparatus for feeding fluids to internal body organs. An implant is introduced subcutaneously comprising a capsule having a hollow interior cavity and at least one channel extending outwardly therefrom. The capsule is puncturable by needle injection, so as to be filled with liquid.

8 Claims, 5 Drawing Figures

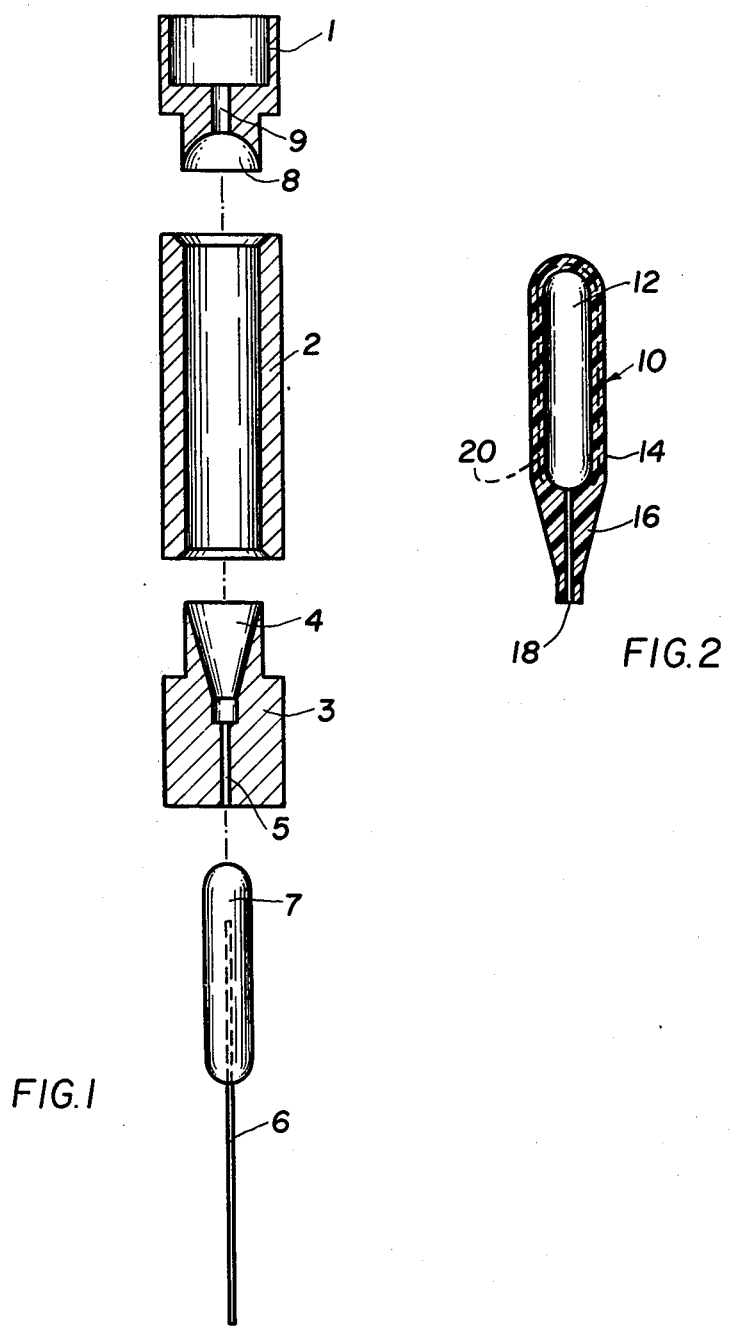

METHOD AND APPARATUS FOR INTRODUCING FLUIDS INTO THE BODY

This application is continuation-in-part of application Ser. No. 335,745 filed Feb. 26, 1973, now abandoned.

BACKGROUND OF INVENTION

The present invention relates to a method and apparatus for introducing fluids into the body and in particular to an implant in which the introduction of liquid by injection can be facilitated.

Recent clinical procedures have shown a rising interest in the therapeutic methods which employ synthetic inlet or outlet tubes extending through the patient's skin to an internally situated organ or substitute organ implant. Such procedures maintain a continuously open wound in the body even though the introduction of fluid through the inlet tube may be periodically administered. In many cases the period between successive injections of fluid may be as long as several days or weeks apart. The open wound, however, requires constant attention and medical administration in order to maintain it free from infection and disease.

In many cases the body organ or its substitute implant is remote from the surface of the body and excessively long tubes must be provided extending from the skin to the situs of the organ. Such arrangements are subject to even greater possibility of infection and the existence of a tube extending outwardly of the body is both annoying and dangerous to the patient.

It is the object of the present invention to provide improved apparatus for use in the implant therapy which overcomes the disadvantages of the prior art. It is the further object of the present invention to provide an improved apparatus and method for feeding fluids to the interior of the body and in particular to internal organs and their substitute implants.

It is a further object of the present invention to provide a capsule which may be subcutaneously implanted in the body after which the body may be closed and fee of any open wound.

The foregoing objects, others and numerous advantages will be seen from the following disclosure of the present invention.

SUMMARY OF THE INVENTION

Briefly, according to the present invention long term tubular outlets through the skin are replaced by an implant introduced into a subcuticular ligament immediately below the skin. Preferably the implant is in the shape of a capsule or pouch formed of a wall construction which substantially retains its shape either when filled or empty and which defines a hollow interior cavity of substantially constant volume in which the liquid may be stored and which is easily filled through injection with a hypodermic needle or the like. The capsule is provided with at least one channel which may be connected to an implanted tube leading to the body organ or organ substitute. Even though it may be remote from the skin or from the location of the capsule.

In the use of the present invention the skin, after introduction of the implanted capsule can be completely sutured and closed thus avoiding maintaining an open wound. After implantation, the penetration by a sterile and safe needle can be made without forming any permanent or lasting wound. The capsule forms a reservoir for the medicinal fluid and the fluid may be thereafter released in a controlled manner to the situs of the body organ or its implanted substitute. Connection of the capsule to more than one remote body organ and particularly to body organs which would be otherwise highly inaccessable can be made from one container thus eliminating the need for providing several openings into the body.

Typical but not exclusive examples of the applications to which the present invention can be put include the location of the subcutaneous capsule in connection with: implanted organs for the surface diffusion of chemical drugs, etc. (eg.: cytostatics) deliverable to tumors, cancerous tissues, etc., in accordance wth Czechoslovak patent 157213, application PV114-71, and the corresponding U.S. application Ser. No. 210,420; arteries in deep or remote positions so that precisely oriented diffusion of drugs can be made; the connection of a capsule to an artery on the one hand and the same container or a different container to a vein on the other hand enabling the periodic circulation of blood to be made through an extracorporeal diffusion device such as an artificial kidney, and; to a peritoneal cavity for peritoneal dialysis.

Full details of the present invention are set forth hereinafter and are depicted in the accompanying drawings.

BRIEF DESCRIPTION OF THE DRAWINGS

In the drawings:

FIG. 1 is an expanded view of mold apparatus employed to form the device of the present invention, FIG. 2 is a view of the apparatus of the present invention.

DESCRIPTION OF INVENTION

Figures 3, 5:
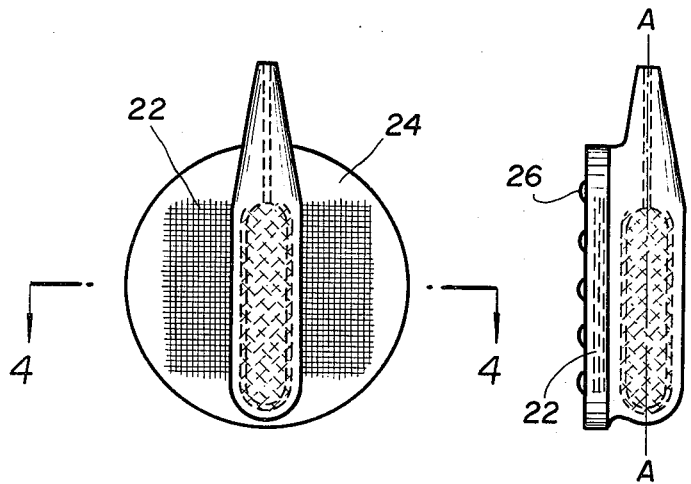
FIG. 3 is a view of the apparatus according to the present invention having a reinforcing wall inpenetrable to puncture by a needle or the like, FIG. 4 is a sectional view of along line 4—4, transverse to the central axis of FIG. 3
FIG. 5 is a sectional view along the central axis 5—5 of FIG. 3.

As seen in FIGS. 2, 3 and 5 the capsule takes the form of a non-collapsible pouch generally defined by the numeral 10 which is to be implanted immediately below the skin to provide a capsule and connection between the surface and the internal organ. The pouch has a simple configuration comprising a generally enclosed body in the shape of an oblong capsule having a hollow interior cavity 12. A spherical, elliptical or other configuration may also be used. The capsule has a substantially unitary thick wall 14 so that it is self-supporting and will maintain its shape and volume even in a totally empty or unfilled condition. The thickness of the wall is a function of the material, its strength and the permeability characteristics desired for any particular use and may thus clearly chosen empirically. The wall is devoid of any openings, ports, nodules or exterior or interior supports. It terminates in a thickened or enlarged neck portion 16 which extends outward from one end of the oblong body. A channel 18 passes through the neck 16 opening from the hollow interior cavity 12 to the exterior. The neck 16 is preferably narrowed at its outer end to provide a nipple to which a tube or similar conduit may be connected. The tube is adapted to lead to one or more of the internal body organs or their implanted substitutes. Thus fluid stores in the interior cavity 12 can be dispersed directly to the organs, which are to be treated.

The capsule walls are formed from elastic materials capable of being self resealable and of sufficient thickness or form so as to be easily penetratable by needle but not flexible so as to collapse. In any event the material chosen must be readily puncturable over extended periods of time without degradation or becoming porous. If it is desired a reinforcement 20 of textile fibers or fabric sheet can be imbedded in the walls 14 of the capsule surrounding the cavity 12. Because the thickened neck is mechanically stronger than the remaining portion of the wall the reinforcement need not be placed within its area if it is so desired. The textile fibers and/or fabric making up the reinforcement should be of such open construction that it be easily penetrable by the needle or other injection instrument.

Figure 4:
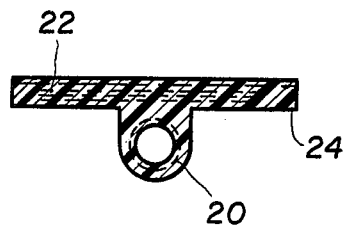

In the embodiment shown in FIGS. 3 to 5 a reinforced wall 22 is imbedded with the body to one side of the cavity 12. This side is preferably opposite to that in which injection is to be made when the capsule is subcutaneously located. This wall 22 is constructed to be impenetrable by a needle or other injection apparatus and thus provides a barrier preventing the injection apparatus from passing through both walls of the capsule to inadvertently discharge its fluid directly into the body of the patient.

To insure that the wall 22 acts as a successful barrier the capsule is best made of a size and shape wherein its longest dimension lies in a plane parallel to that of the reinforcing wall 22 and that this dimension is substantially longer than the dimensions lying in planes which are perpendicular to it. In the oblong configuration of FIGS. 3 through 5 the longest dimension lies along the line A—A which is parallel to the axis of the reinforcing wall 22 thus the wall fully covers the entire length of the capsule.

As seen further from FIGS. 3 through 5 the back side of the capsule is provided with an enlarged flap 24 which may be advantageously circular although other shapes may also be used. The flap extension 24 is preferably reinforced with a fabric interior and is larger than the container itself. This enlargement of the capsule serves to prevent it from rotating within the body of the patient after implantation or from moving away from its initial subcutaneous location. This is a very important attribute particularly when the capsule may be otherwise symetrically shaped as shown in the figures. If desired the flap extension may be sutured or suitably connected to the body tissue beneath the surface of the skin thereby further insuring that the capsule is held in place. The flap may also be provided with one or more horizontal or transverse ridges 26 which increase frictional holding power once implanted.

The material from which the subcutaneous capsule of the present invention can be made may be chosen from any elastomeric substance which is tolerated by the body and which will not react with the live tissue or body fluids with which it may come in contact. Such inert substances are now common in medical fields and may include although are not necessarily limited thereto to: silicon rubber; butyl rubber; natural rubber, alone or coated with a film of hydrophylic material well tolerated by the body; hydrophylic gels which are highly swellable in water or in physiological solutions and other body fluids. The last group of materials, namely the hydrophylic gels include the glycol acrylate and methacrylate polymers. The elastic polymers possess the desirable property that they may be repeatedly punctured and penetrated by sharp instruments such as hypodermic needles and other injection apparatus and yet spontaneously and perfectly reseal itself to maintain a continuous and tight non-leaking wall. A danger may exist that after extensive puncturing the material may tend to become very weak and be damaged to a degree rendering it mechanically unusable. In this case however, such material may be strengthened by increasing its mechanical properties through the use of suitable filler material such as textile fibers or by the use of a layer of textile fabric which act as reinforcement. Organic or inorganic textile materials may be used. The reinforcement may, depending upon its use, be porous or nonporous and may include materials such as metals, plastics or synthetics as well as glass in sheet, fiber, woven or nonwoven form.

The barrier wall 22 through which complete penetration of the injection means can be prevented, may be formed by several layers of fabric material or by the use of metal or glass sheets as well as of synthetic material.

While the pouch may be formed in conventional manner, a preferred form of a mold and casting system is provided which greatly facilitates the construction of the apparatus. As seen in FIG. 1 the mold comprises an upper section 1, a central section 2, and a lower section 3. The central section 2 comprises a hollow cylinder having an inner surface conforming generally to the shape of the wall 14 of the capsule seen in FIG. 2. If it is desired to produce the capsule of FIGS. 3 through 5, the central section may be correspondingly cut out to provide the enlarged extension areas needed to accommodate the flap portion 24 and the reinforcing and barrier wall 22. The lower section 3, adapted to plug into the central section 2 is provided with a conical interior surface 4 adapted to conform to the shape of the neck 16 of the capsule. Extending from the conical surface 4 is a bore 5 through which a stainless steel wire 6 is adapted to be inserted. Prior to the closing of the mold the stainless steel wire is provided with an oblong core 7 carried at its end. The core is made of paraffin wax or other suitable disintegratable material employed in molding procedures and conforms to the shape of the interior cavity 12 of the capsule. The paraffin core is inserted within the central section 2 and spaced from its interior walls. The reinforcing textile fabrics 20 and barrier walls 22 may then be inserted between the paraffin core and the wall of the section 2. The upper section 1 comprises a charging plug for the central section through which the elastomeric material may be fed to it. The section 1 has a hemispherical section 8 which conforms to the end of the capsule and which seats within the upper end of the section 2. A charging inlet duct 9 is provided through which the elastomeric material passes.

The following examples of the formation of the capsule are given to illustrate the present invention. They are to be taken as illustrative only and not limiting of the many examples possible.

EXAMPLE I

Employing the mold shown in FIG. 1 a tubular knitted fabric made of Terylene yarn having a diameter corresponding to the inner diameter of the central section 2 is inserted within that section prior to the insertion of the paraffin core 7. The mold is then assembled as indicated above. After assembly a monomeric charge which polymerizes at a temperature below that of the paraffin is poured into the mold. The charge comprises a mixture of 65 parts by weight of hydroxyethyl methacrylate, 0.2 parts by weight of ethylene dimethacrylate, 17.5 parts by weight of a 1% aqueous solution of ammonium persulfate and 17.5 parts by weight of a 1% aqueous solution of sodium pyrosulfate. The mixture is heated to 35°C. for about 20 minutes, converting it into a gel. Polymerization is completed by heating the gel for 5 minutes longer at 100°C., which also melts the paraffin wax. After suitable cooling the mold is thereafter disassembled and the wire 6 withdrawn from the thus formed capsule. By squeezing the capsule the melted paraffin wax is extruded from within the interior cavity 12. Flashing corresponding to the inlet hole 9 is removed and the capsule washed thoroughly in water and boiled in a physiological saline solution until thoroughly cleaned. The elastomeric polymer formed is a hydrophylic gel highly swellable in water or similar solutions. The capsule formed conforms to that shown in FIG. 1 and may be used for any of the purposes hereinbefore described.

EXAMPLE II

The mold shown in FIG. 1 is modified to provide a cutout extension adapted to conform to the flap 24 of the capsule shown in FIGS. 3 through 5. In a similar manner the textile reinforcement 20 is inserted into the central section 2 after which the paraffin wax core is also inserted. The barrier wall 22 is formed by several layers of thick Terylene fabric which are inserted between the reinforcement 20 and the outer wall of the flap extension of the mold. The mold is closed and filled with the elastomeric monomeric mixture which is polymerized in accordance with Example 1. The resultant container is characterized by the fact that it has a barrier wall in addition to the thin textile reinforcement surrounding the cavity 12. It otherwise corresponds to that described earlier and may be used for the same uses.

In the foregoing examples the mold is preferably made from Teflon or other suitable synthetic material capable of use in such a molding procedure. The Teflon may be used to coat the interior surface or the entire body of the sections of the mold may be made from it.

Various changes and modifications may be made to the foregoing method as well as to the apparatus as finally completed. Many of these changes have been described herein, others will be obvious to those skilled in the art. The present disclosure therefore is intended to be illustrative only and not limiting of the invention in any manner.

What is claimed:

1. Apparatus for supplying fluids in an interior body organ comprising a capsule adapted to be implanted subcutaneously for extended periods of time said capsule having unitary walls formed of substantially non-collapsable self-sealing elastic material penetrable by injection and defining an enclosed bulbous interior cavity of given volume for receipt of fluid, said walls being formed of a hydrophillic elastic gel of sufficient strength to retain its shape and maintain a constant volume during periodic filling and emptying and reseal itself under penetration by injection feeding while implanted, said capsule having a channel exiting therefrom for connection to a conduit for the feeding and withdrawal of fluids to some body organ.

2. The apparatus according to claim 1, wherein a penetrable textile is imbedded within said elastic material to reinforce the same.

3. The apparatus according to claim 2, wherein the reinforcement is in the form of a penetrable textile fabric surrounding said cavity.

4. The apparatus according to claim 1, including an impenetrable wall imbedded in said material to one side of said cavity providing a barrier against injection through a portion of said capsule.

5. The apparatus according to claim 4 wherein said capsule is formed so that its dimension in the plane parallel with said wall is substantially larger than in the planes perpendicular thereto.

6. The apparatus according to claim 1, including extension means located on the exterior of said capsule for fixing and fixedly locating said capsule in the body.

7. The apparatus according to claim 1, wherein said capsule is shaped as a hollow oblong capsule having an enlarged neck at one end through which said channel passes, said neck having means for connection of a tube thereto.

8. The method of supplying fluid to body organs comprising the steps of implanting subcutaneously a hollow capsule capable of being injected with a fluid, said capsule having at least one exiting channel and connecting to said channel a conduit leading to said body organ.

* * * * *